US00PP12741P2

(12) United States Plant Patent
Dümmen

(10) Patent No.: US PP12,741 P2
(45) Date of Patent: Jul. 2, 2002

(54) NEW GUINEA IMPATIENS PLANT NAMED 'DUERIBLUNI'

(75) Inventor: Marga Dümmen, Rheinberg (DE)

(73) Assignee: Dümmen Jungpflanzenkulturen, Rheinberg (DE)

( * ) Notice: Subject to any disclaimer, the term of this patent is extended or adjusted under 35 U.S.C. 154(b) by 0 days.

(21) Appl. No.: 09/512,636

(22) Filed: Feb. 25, 2000

(51) Int. Cl.[7] ..... A01H 5/00

(52) U.S. Cl. ..... Plt./318

(58) Field of Search ..... Plt./318

*Primary Examiner*—Bruce R. Campell
*Assistant Examiner*—Michelle Kizilkaya
(74) *Attorney, Agent, or Firm*—C. A. Whealy

(57) ABSTRACT

A new and distinct cultivar of New Guinea Impatiens plant named 'Dueribluni', characterized by its large purple-colored flowers; freely flowering habit with flowers positioned above the foliage; upright, mounded, densely foliated and freely branching plant habit; and dark green leaves.

1 Drawing Sheet

BACKGROUND OF THE INVENTION

The present Invention relates to a new and distinct cultivar of New Guinea Impatiens plant, botanically known as *Impatiens hawkeri*, and hereinafter referred to by the cultivar name Dueribluni.

The new Impatiens is a product of a planned breeding program conducted by the Inventor in Rheinberg, Germany. The objective of the breeding program was to develop new New Guinea Impatiens cultivars with large flowers and interesting flower and foliage colors.

The new Impatiens originated from a cross made by the Inventor of the *Impatiens hawkeri* selection identified as D5, not patented, as the male, or pollen parent, with the *Impatiens hawkeri* selection identified as K20P, not patented, as the female, or seed parent. The cultivar Dueribluni was discovered and selected by the Inventor as a flowering plant within the progeny of the stated cross in a controlled environment in Rheinberg, Germany. Plants of the new Impatiens differ from plants of the male parent, the selection D5, in vigor and foliage color. Plants of the new Impatiens differ from plants of the female parent, the selection K20P, in plant habit and flower color.

Asexual reproduction of the new cultivar by terminal cuttings taken at Rheinberg, Germany, has shown that the unique features of this new Impatiens are stable and reproduced true to type in successive generations.

SUMMARY OF THE INVENTION

The following traits have been repeatedly observed and are determined to be the unique characteristics of 'Dueribluni'. These characteristics in combination distinguish 'Dueribluni' as a new and distinct cultivar:

1. Large purple-colored flowers.
2. Freely flowering habit.
3. Flowers positioned above the foliage.
4. Upright and mounded plant habit.
5. Freely branching habit.
6. Dark green leaves; densely foliated.

Compared to plants of the commercial New Guinea Impatiens cultivar Aruba, disclosed in U.S. Plant Pat. No. 8,456, plants of the new Impatiens have a more uniform plant habit and darker flower color.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which more accurately describe the actual colors of the new Impatiens. The photograph comprises a side perspective view of a typical flowering plant of 'Dueribluni'.

DETAILED BOTANICAL DESCRIPTION

The cultivar Dueribluni has not been observed under all possible environmental conditions. The phenotype may vary somewhat with variations in environment such as temperature and light intensity, without, however, any variance in genotype. The aforementioned photograph, following observations and measurements describe plants grown in Rheinberg, Germany, under commercial practice in a glass-covered greenhouse with day and night temperatures about 18° C. and light levels generally about 4,500 lux. Plants used in the photograph and description were about 14 weeks old.

In the following description, color references are made to The Royal Horticultural Society Colour Chart except where general terms of ordinary dictionary significance are used.

Botanical classification: *Impatiens hawkeri* cultivar Dueribluni.

Parentage:

*Male parent.*—*Impatiens hawkeri* selection identified as D5, not patented.

*Female parent.*—*Impatiens hawkeri* selection identified as K20P, not patented.

Propagation:

*Type cutting.*—Terminal cuttings.

*Time to initiate roots.*—Summer: About 10 days at 22° C. Winter: About 12 days at 22° C.

*Time to produce a rooted cutting or liner.*—Summer: About 21 days at 22° C. Winter: About 24 days at 22° C.

*Rooting habit.*—Numerous, freely branching and thick.

Plant description:

*General appearance.*—Upright and mounded. Appropriate for 10 to 15-cm containers.

*Growth and branching habit.*—Very freely branching with about 22 lateral branches at the base, dense and bushy growth. Pinching, that is, removal of the terminal apices, is typically not required. High growth rate.

*Crop time.*—From an unrooted cutting, about 14 weeks are required to produce a finished flowering plant in a 12 or 13-cm container.

*Plant height.*—About 21 cm.

*Plant spread.*—About 32 cm.

*Lateral branches.*—Length: About 9 cm. Diameter: About 7.2 mm. Internode length: About 3.6 cm. Color: 53A.

*Foliage description.*—Leaves abundant, densely foliated. Arrangement: Alternate or in whorls, simple. Quantity of leaves per lateral branch: About 17. Length: About 8.5 cm. Width: About 3 cm. Shape: Elliptic. Apex: Apiculate. Base: Attenuate. Margin: Serrulate with ciliation. Texture: Smooth. Color: Young foliage, upper surface: 139A. Young foliage, lower surface: 53B. Fully expanded foliage, upper surface: 131A. Fully expanded foliage, lower surface: 183C with spots between 148C and 147B. Venation, upper surface: 185A. Venation, lower surface: 53A. Petiole: Length: About 1.7 cm. Diameter: About 3 mm. Color: Upper surface: 53C. Lower surface: 53A.

Flower description:

*Flower type and flowering habit.*—Large single purple flowers; freely flowering. Usually about 6 to 7 flowers and flower buds per lateral branch and about 120 flowers and flower buds on a mature plant. Flowers positioned above the foliage and typically face outward to upward. Flowers generally flat and rounded. Flowers last about 12 days on the plant depending on temperature and weather conditions. Flowers self-cleaning. Flowers not fragrant.

*Flowering season.*—Year-round under greenhouse conditions. In the garden, flowering from spring until fall. Flowering intermittent.

*Flower diameter.*—About 7.1 cm.

*Flower depth.*—About 3.5 cm.

*Flower buds.*—Rate of opening: From showing color to fully open flower, typically about 2 to 3 days depending on temperature. Length: About 1.7 cm. Diameter: About 8 mm. Shape: Ovoid. Color: 67B.

*Petals.*—Quantity: Single, five per flower. Length: About 3.2 cm. Width: About 4 cm. Shape: Obcordate. Apex: Emarginate to cordate. Base: Acute. Margin: Entire. Texture: Smooth; shiny. Color: When opening, upper surface: 74A. When opening, lower surface: 74B. Fully opened, upper surface: 74A. Fully opened, lower surface: 74B.

*Spur.*—Length: About 4.6 cm. Color: 53A.

*Peduncles.*—Length: About 3.5 cm. Strength: Strong. Aspect: Upright to angled outwardly. Color: 46A.

*Reproductive organs.*—Androecium: Stamen number: 5. Anther shape: Oval. Anther size: About 5 mm. Anther color: 67B. Amount of pollen: Moderate to abundant. Pollen color: 157A. Gynoecium: Pistil length: About 7 mm. Stigma color: 132A. Ovary color: 132A to 132B.

Disease resistance: Resistance to known pathogens of New Guinea Impatiens has not been observed.

Seed development: Seed production has not been observed.

It is claimed:

1. A new and distinct cultivar of New Guinea Impatiens plant named 'Duerribluni', as illustrated and described.

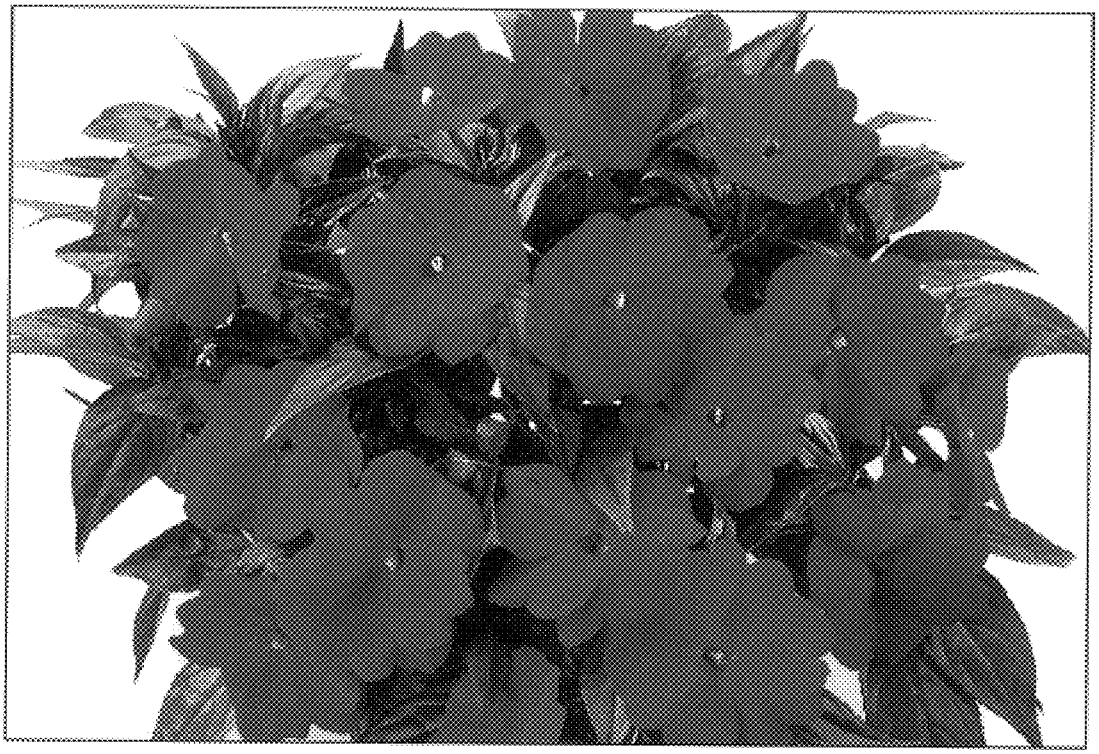

* * * * *